United States Patent [19]
Faeser

[11] Patent Number: 4,931,041
[45] Date of Patent: Jun. 5, 1990

[54] INFUSION SYRINGE PUMP

[75] Inventor: Ulrich Faeser, Kronberg, Fed. Rep. of Germany

[73] Assignee: Fresenius AG, Fed. Rep. of Germany

[21] Appl. No.: 271,975

[22] Filed: Nov. 15, 1988

[30] Foreign Application Priority Data

Nov. 22, 1987 [DE] Fed. Rep. of Germany ....... 3739563

[51] Int. Cl.$^5$ ............................................ A61M 37/00
[52] U.S. Cl. ............................... 604/155; 128/DIG. 1
[58] Field of Search .................... 604/66, 67, 154, 155; 128/DIG. 1

[56] References Cited

U.S. PATENT DOCUMENTS 3,701,345 10/1972 Heilman et al. ............... 128/DIG. 1
4,399,712 8/1983 Oshikubo et al. .................... 604/155
4,802,487 2/1989 Martin et al. .................. 128/662.06

Primary Examiner—Jerome L. Kruter
Attorney, Agent, or Firm—Henderson & Sturm

[57] ABSTRACT

The invention relates to an infusion syringe pump which by means of a motor-gear unit drives a linearly movable drive member which is in engagement with the syringe plunger of an infusion syringe. According to the invention a position-defining element is connected only to the linearly movable drive member which actuates the syringe plunger of the infusion syringe. The position-defining element is functionally coupled to an absolute displacement pickup which is preferably constructed as linear potentiometer. By the control means according to the invention the absolute position of the syringe plunger can be determined.

5 Claims, 1 Drawing Sheet

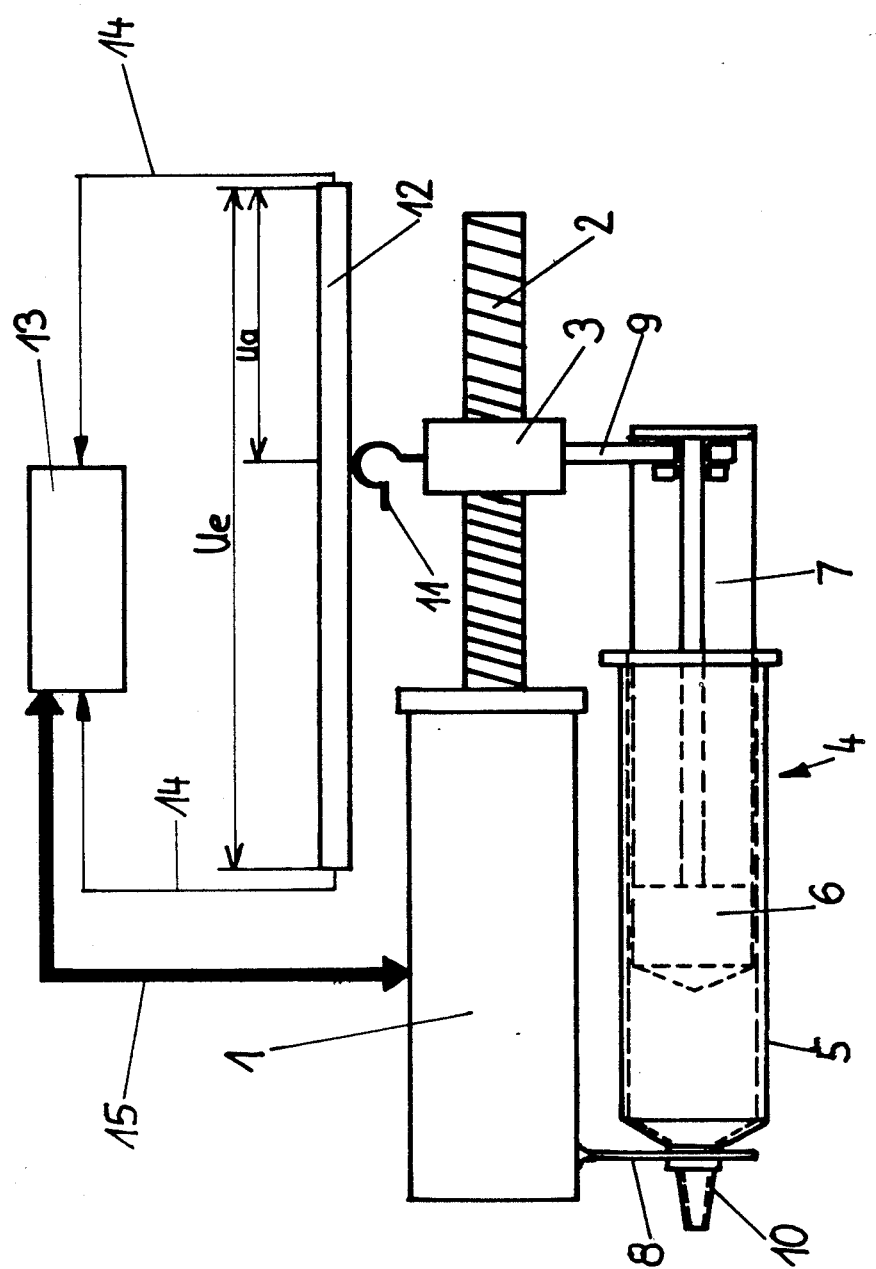

INFUSION SYRINGE PUMP

BACKGROUND AND SUMMARY OF THE INVENTION

The invention relates to an infusion syringe pump comprising a motor-gear unit for driving a linearly movable drive member, an injection syringe having a syringe plunger which for its actuation is in engagement with the drive member and a position detecting means for determining the position of the syringe plunger, said means having a position-defining element and a stationary absolute displacement pickup.

DE-OS 2,922,037 and DE-GM 8,520,376 disclose syringe pumps which operate with optoelectronic detection means. These detection means have the disadvantage that it is not possible to produce a continuous signal so that the accuracy of the position detection is a function of the respective code-dependent quantization of the optoelectronic elements.

US-PS 4,620,848 discloses an infusion syringe pump in which a first roller mounted stationarily on a housing is in engagement with a syringe plunger which in turn is driven by a motor, a gearing and a second roller whih is also mounted on the housing and which is drivingly connected to the motor via the gearing. The first roller, which is rotationally driven, is mounted on the housing and not on the drive member for the syringe plunger.

Furthermore, an infusion syringe pump is known from US-PS 3,701,345 in which a motor drives a plunger for expelling the fluid from a syringe cylinder. This angiographic infusion syringe pump comprises a position control system which employs a feedback voltage signal which is not associated with the syringe plunger speed but with the infusion syringe plunger position. Said feedback signal is generated by a mechanically driven potentiometer which is set in operation by the drive motor via an additional gearing. Before performing the injection the instantaneous position of the syringe plunger is sensed and the position thereof used as basis reference quantity or zero limit. The desired injection volume, corresponding voltage limits or the desired rate are predefined proportionally to the voltage by the operator.

As mentioned above, in this system a potentiometer is used to detect the instantaneous position of the syringe plunger. The position signal is compared with a control signal and the resulting difference used to operate the motor. The motor is influenced by a voltage-limiting circuit which prevents the motor delivering too much power. On return of the syringe plunger into its initial position the direction of rotation of the motor and thus of the gearing is reversed. In such infusion syringe or injection pumps in which the injection or syringe plunger is returned to its initial position in dependence upon the motor-gear unit by reversal of the direction of rotation of the motor it is admittedly possible to determine at any time an instantaneous absolute position value of the syringe plunger; however, the construction of the position control system is made complicated by the necessity of an additional gearing transmission for the position control system. The presence of an additional gearing transmission can moreover introduce a source of error into said control system because inaccuracies or errors of the additional gearing transmission can give rise to a deviation of the actual position of the syringe plunger in the syringe cylinder from the position information supplied by the position control system.

In addition, such a pump is complicated in manipulation because the entire drive arrangement must be moved to the initial state when a new (filled) syringe is to be inserted.

In other known infusion injection or syringe pumps in which the injection or syringe plunger can be returned to its zero position independently of the motor-gear unit, such as for example described in DE-OS 3,428,655, it would be desirable to have such a position value determination.

According to the invention the problem is solved in that the position-defining or position-indicating element is rigidly connected to the linearly movable drive member, and that the position-defining element along its path of movement corresponding to the displacement direction of the drive member is electrically or magnetically coupled to the absolute displacement pickup.

In a preferred embodiment the absolute displacement pickup is constructed as linear potentiometer.

In addition, the absolute displacement pickup may be a capacitive or magnetic position-defining element.

Furthermore, the absolute displacement pickup is connected to an evaluating unit.

Due to the preferably rigid connection of the position-pickup element to the drive member driving the syringe plunger the possible source of error of the defective auxiliary gear in US-PS 3,701,345 can be eliminated. Consequently, due to the direct tapping off of the instantaneous plunger position extensive freedom from error can be ensured.

Infusion syringe pumps which can move the syringe plunger into any desired initial position independently of the motor-gear unit can be provided with a drive spindle leading to the motor-gear unit and a drive member which by an actuating element can be disengaged from the drive spindle by rotation about its longitudinal axis and thus pulled forwardly or rearwardly independently of the motor-gear unit, as is the case in DE-OS 3,428,655. By reengagement of the drive member the latter can be locked again in any desired position.

Due to the fixed connection the position-indicating or position-pickup element is displaced with the drive member and correlated thereto represents the position of the drive member and thus the syringe plunger.

The invention will be explained in detail hereinafter with the aid of an example of embodiment.

DESCRIPTION OF THE DRAWING

The enclosed drawing shows an infusion syringe pump according to the invention in which the syringe plunger is movable independently of the motor-gear unit into any desired initial position.

DETAILED DESCRIPTION OF A PREFERRED EMBODIMENT OF THE INVENTION

The infusion injection pump comprises a motor-gear unit 1 which drives a threaded spindle 2 which projects from an end face of the motor-gear unit 1 and on which a linearly movable drive member 3 is disposed.

The infusion syringe 4 consists of a syringe cylinder 5 and a syringe plunger 6 having a plunger rod 7. The front end of the syringe cylinder 5 is inserted into a holder 8 which in the case of the example is mounted on the motor-gear unit 1 of the infusion syringe pump. The rear end of the plunger rod 7 is inserted into a further holder 9 which is disposed on the linearly movable drive member 3. If the linearly movable drive member 3 is moved in the direction towards the motor-gear unit 1 the syringe plunger 6 in the syringe cylinder 5 is displaced and the injectate is expelled through the syringe outlet 10. The syringe outlet is connected via a (not shown) flexible tube to the patient.

Such an infusion syringe pump is described in DE-OS 3,428,655, to the disclosure of which reference is made.

A position-defining element 11 is arranged on the linearly movable drive member 3 in such a manner that said element is coupled functionally to an absolute displacement pickup 12, in particular is in engagement therewith. Said absolute displacement pickup 12 is constructed in a particular embodiment of the invention as linear potentiometer as shown in the drawing. The absolute displacement pickup 12 may also be formed by a known inductive capacitive or magnetic position-indicating element.

As also apparent from the drawing the absolute value pickup 12 extends parallel to the longitudinal axis of the threaded spindle 2 or to the displacement direction of the drive member 3.

Furthermore, the absolute displacement pickup 12 is connected to an evaluating unit 13 via the line 14 which in turn is connected via a line 15 to the motor-gear unit 1.

Likewise, the ends of the linear potentiometer are connected via the lines 14 to the evaluating unit 13 and form together with the position-defining element 11 a voltage divider, said element 11 being formed as wiping contact.

The evaluating unit 13 defines the input voltage $U_e$ of the absolute displacement pickup 12, that is the linear potentiometer, and at the same time stores said voltage. The position-defining element 11 on the linearly movable drive member 3 is now also at a predetermined position of the linear potentiometer which at this point taps off a certain output voltage signal $U_a$ and passes said signal to the evaluating unit 13. Said output voltage $U_a$ is proportional to the position of the position-defining element 11 and thus to the instantaneous position of the syringe plunger 6 in the syringe cylinder 5 and after corresponding conversion indicates the coordinates thereof on the movement or position axis.

Infusion pumps are usually designed for a certain type of syringe or injection needle and for technical safety reasons only approved for one such type. Consequently, the output voltage $U_a$ indicates for the approved syringe type the absolute coordinate of the syringe plunger provided the syringe is properly inserted into the receiving means 8 and 9.

On the other hand, after appropriate calibration another type of syringe can however also be employed.

The necessary and usual infusion-relevant parameters are centered into the evaluating unit before and during the infusion operation. Consequently, the value tapped off at the linear potentiometer can itself indicate the remaining amount of infusion in the syringe 5 or, via the entered advance rate, the remaining infusion time.

The circuits and components of the evaluating unit 13 correspond to the state of the art.

Moreover, the evaluating unit 13, as indicated in the drawing by the line 15, can also be used for controlling the motor-gear unit 1.

I claim:

1. Infusion syringe pump comprising:
    a motor-gear unit and a threaded spindle for driving a linearly movable drive member,
    an injection syringe having a syringe plunger which for its actuation is in engagement with the drive member and
    a position detecting means for determining the position of the syringe plunger, said means having a position-defining element and a stationary absolute displacement pickup extending along the length of said threaded spindle,
    characterized in
    that the position-defining element is rigidly connected to the linearly movable drive member, and
    that the position-defining element along its path of movement corresponding to the displacement direction of the drive member is electrically coupled to the absolute displacement pickup.

2. Infusion syringe pump according to claim 1, characterized in that the absolute displacement pickup is constructed as linear potentiometer.

3. Infusion syringe pump according to claim 1, characterized in that the absolute displacement pickup is constructed as inductive, capacitive or magnetic position-defining element.

4. Infusion syringe pump according to claims 1, 2 or 3, characterized in that the absolute displacement pickup is connected to an evaluation unit.

5. Infusion syringe pump according to claim 1 wherein said position defining is magnetically coupled to said absolute displacement pickup.

* * * * *